(12) United States Patent
Asogawa et al.

(10) Patent No.: US 11,873,476 B2
(45) Date of Patent: Jan. 16, 2024

(54) MICROCHIP, MICROCHIP CONTROLLING APPARATUS AND MICROCHIP CONTROLLING SYSTEM

(71) Applicant: NEC Corporation, Tokyo (JP)

(72) Inventors: Minoru Asogawa, Tokyo (JP); Yasuo Iimura, Tokyo (JP); Yoshinori Mishina, Tokyo (JP)

(73) Assignee: NEC CORPORATION, Tokyo (JP)

( * ) Notice: Subject to any disclaimer, the term of this patent is extended or adjusted under 35 U.S.C. 154(b) by 198 days.

(21) Appl. No.: 17/364,194

(22) Filed: Jun. 30, 2021

(65) Prior Publication Data

US 2021/0324323 A1 Oct. 21, 2021

Related U.S. Application Data

(63) Continuation of application No. 15/506,015, filed as application No. PCT/JP2015/073960 on Aug. 26, 2015, now Pat. No. 11,066,636.

(30) Foreign Application Priority Data

Aug. 29, 2014 (JP) ................. 2014-176340

(51) Int. Cl.
C12M 1/00 (2006.01)
G01N 35/08 (2006.01)
G01N 37/00 (2006.01)

(52) U.S. Cl.
CPC ............. *C12M 47/06* (2013.01); *C12M 1/00* (2013.01); *G01N 35/08* (2013.01); *G01N 37/00* (2013.01)

(58) Field of Classification Search
None
See application file for complete search history.

(56) References Cited

U.S. PATENT DOCUMENTS

| | | | |
|---|---|---|---|
| 3,799,742 A | 3/1974 | Coleman | B01L 3/502753 422/417 |
| 5,290,518 A | 3/1994 | Johnson | B01L 3/502 422/413 |
| 2002/0045246 A1* | 4/2002 | McMillan | C12M 47/06 435/306.1 |
| 2003/0027352 A1 | 2/2003 | Hooper | B82Y 30/00 436/169 |

(Continued)

FOREIGN PATENT DOCUMENTS

| EP | 2657708 A1 | 10/2013 |
|---|---|---|
| EP | 2847434 A1 | 10/2013 |

(Continued)

OTHER PUBLICATIONS

International Search Report for PCT Application No. PCT/JP2015/073960, dated Nov. 10, 2015.

(Continued)

*Primary Examiner* — Lore R Jarrett
(74) *Attorney, Agent, or Firm* — Sughrue Mion, PLLC

(57) ABSTRACT

A microchip includes a cell accepting section, a lysis solution chamber and a lysis reaction chamber. The cell accepting section accepts cells obtained from a subject. The lysis solution chamber stores lysis solution for lysis of the cells. The lysis reaction of the cells is executed in the lysis reaction chamber.

1 Claim, 8 Drawing Sheets

(56) References Cited

U.S. PATENT DOCUMENTS

| | | | |
|---|---|---|---|
| 2005/0053952 A1* | 3/2005 | Hong | C12Q 1/6806 435/6.14 |
| 2005/0142565 A1 | 6/2005 | Samper et al. | |
| 2006/0088929 A1* | 4/2006 | Nakajima | F04B 43/046 435/288.5 |
| 2006/0127277 A1 | 6/2006 | Numajiri | G01N 35/08 422/65 |
| 2007/0092876 A1 | 4/2007 | Xu | |
| 2008/0145857 A1 | 6/2008 | Saito et al. | |
| 2010/0105029 A1* | 4/2010 | Ririe | C12Q 1/6806 435/6.12 |
| 2010/0130732 A1 | 5/2010 | Chung | B01L 3/502738 536/25.41 |
| 2010/0297754 A1 | 11/2010 | Solli et al. | |
| 2011/0000561 A1 | 1/2011 | Asogawa | B01L 3/502738 137/561 R |
| 2011/0005932 A1 | 1/2011 | Jovanovich | G01N 21/64 204/453 |
| 2012/0178091 A1 | 7/2012 | Glezer | B01L 3/5027 435/6.12 |
| 2013/0217022 A1 | 8/2013 | Cao et al. | |
| 2013/0248366 A1 | 9/2013 | Haswell et al. | |
| 2014/0079605 A1 | 3/2014 | Asogawa | G01N 35/1095 422/537 |

FOREIGN PATENT DOCUMENTS

| | | |
|---|---|---|
| EP | 2759344 A2 | 7/2014 |
| JP | 2007-534313 A | 11/2007 |
| JP | 2008-586989 A | 2/2008 |
| JP | 2008-148576 A | 7/2008 |
| JP | 2010-529839 A | 9/2010 |
| JP | 2011-528552 A | 11/2011 |
| JP | 2012-529266 A | 11/2012 |
| JP | 2013-537043 A | 8/2013 |
| JP | 2014-507937 A | 4/2014 |
| WO | 2009/119698 A1 | 10/2009 |

OTHER PUBLICATIONS

Japanese Office Action for JP Application No. 2016-545567 dated Dec. 12, 2017 with English Translation.

Extended European Search Report for EP Application No. EP15834976.1 dated Mar. 8, 2018.

* cited by examiner (A)

(B)

(C)

(D)

21: pressure accumulator
22: controller
24: power supplying unit
25: displaying unit

MICROCHIP, MICROCHIP CONTROLLING APPARATUS AND MICROCHIP CONTROLLING SYSTEM

CROSS-REFERENCE TO RELATED APPLICATION

The present application is a Continuation application of Ser. No. 15/506,015 filed on Feb. 23, 2017, which is a National Stage Entry of PCT/JP2015/073960 filed on Aug. 26, 2015, which claims priority from Japanese Patent Application 2014-176340 filed on Aug. 29, 2014, the contents of all of which are incorporated herein by reference, in their entirety.

TECHNICAL FIELD

The present invention relates to a microchip, microchip controlling apparatus and microchip controlling system.

BACKGROUND

Recently, technology in which biochemical reaction, such as PCR (Polymerase Chain Reaction), is executed on a microchip has been developed. For example, Patent Literature 1 discloses a microchip in which sheets (plates) comprising elastic member are laminated.

Patent Literature 1

International application publication No. WO2009/119698A1

SUMMARY

Herein, disclosure in the Prior art document is incorporated into the present application by citation. Analysis described below was made by inventors of the present application.

The microchip disclosed in Patent Literature 1 does not comprise a construction for preparing sample solution. Therefore, in order to carry out DNA (Deoxyribo Nucleic Acid) analysis and the like with the microchip disclosed in Patent Literature 1, it was required for an operator to previously prepare the sample solution in manual operation. Such preparation of the sample solution is a factor of increment of operator's operation.

The present invention was made for a purpose of providing a microchip, microchip controlling apparatus and microchip controlling system contributing to reduce the operator's operation.

According to first aspect of the present invention, there is provided a microchip comprising a cell accepting section accepting cells obtained from a subject, a lysis solution chamber storing lysis solution for lysis of the cells, and a lysis reaction chamber in which lysis reaction of the cells is executed.

According to second aspect of the present invention, there is provided a microchip controlling apparatus comprising: a microchip loading unit on which a microchip comprising a cell accepting section accepting cells obtained from a subject, a lysis solution chamber storing lysis solution for lysis of the cells, and a lysis reaction chamber in which lysis reaction of the cells is executed is loaded; a first lysis solution transferring unit transferring the lysis solution from the lysis solution chamber to the cell accepting section; a second lysis solution transferring unit transferring lysis solution containing the cells from the cell accepting section to the lysis reaction chamber, and a lysis reaction unit heating the lysis solution containing the cells in the lysis reaction chamber for executing the lysis reaction.

According to third aspect of the present invention, there is provided a microchip controlling system consisting: of a microchip comprising a cell accepting section accepting cells obtained from a subject, a lysis solution chamber storing lysis solution for lysis of the cells, and a lysis reaction chamber in which lysis reaction of the cells is executed; and a microchip controlling apparatus comprising a first lysis solution transferring unit transferring the lysis solution from the lysis solution chamber to the cell accepting section, a second lysis solution transferring unit transferring the lysis solution containing cells from the cell accepting section to the lysis reaction chamber, and a lysis reaction unit heating the lysis solution containing the cells in the lysis reaction chamber for executing the lysis reaction.

According to each aspect of the present invention, there are provided a microchip, microchip controlling apparatus and microchip controlling system contributing to reduce operator's operation.

PREFERRED MODES

The present invention is schematically depicted in the figures and described below together with reference to the drawings. Identical components or components having the same function are described with the same symbols in almost cases.

Figure 1:
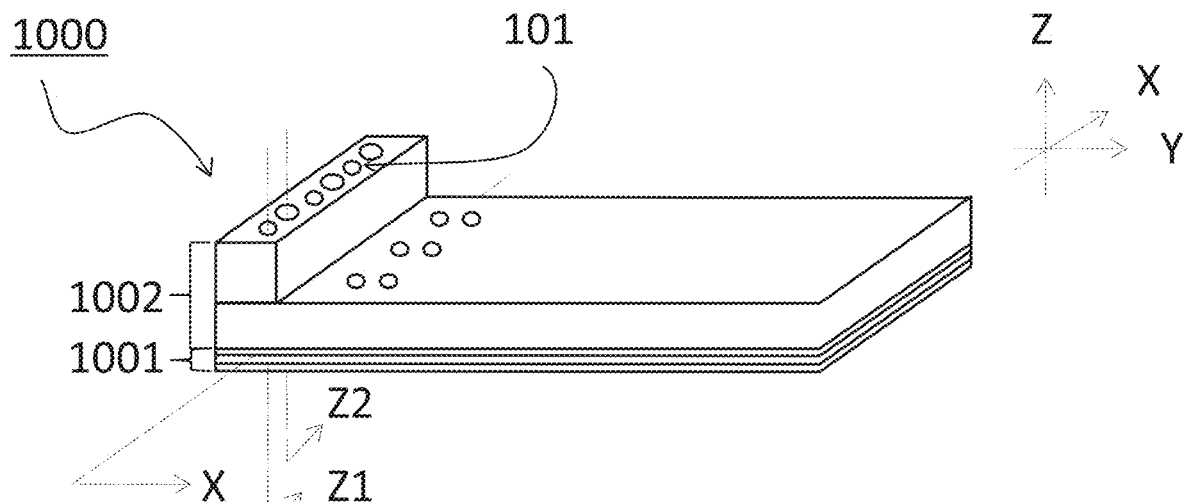
FIG. 1 is a summary diagram of a microchip.
Figure 1:
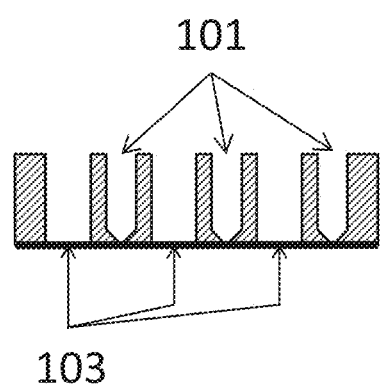
Figure 1:
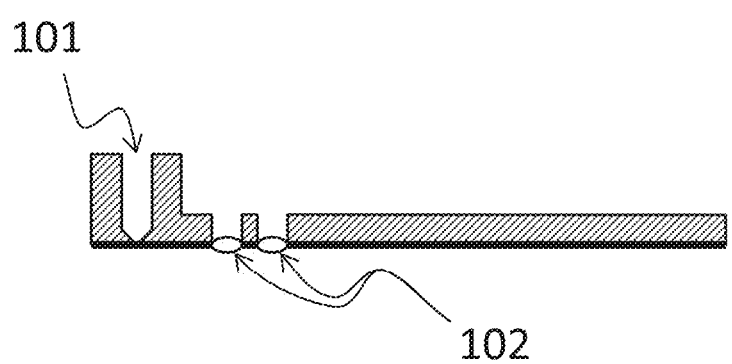
Figure 1:
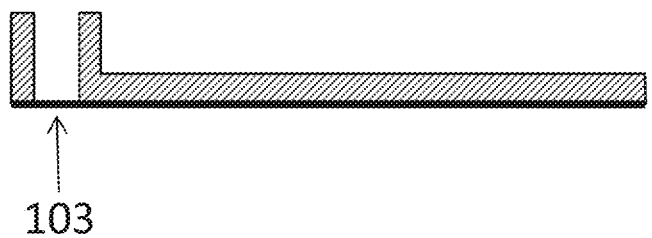

In first, construction of microchip as an exemplary embodiment will be explained. FIG. 1(A) is a perspective view of a microchip 1000. FIG. 1(B) is X axis sectional view of the microchip 1000. FIGS. 1(C), (D) are respectively Z1 axis sectional view and Z2 axis sectional view of the microchip 1000.

The microchip 1000 has a structure in which a plurality of films 1001 and resin plates 1002 are laminated, and comprises a cell accepting section 101 accepting cells obtained from a subject, a lysis solution chamber 102 storing lysis solution for lysis of the cells and a lysis reaction chamber 103 in which lysis reaction of the cells is executed. Herein, the lysis reaction chamber 103 is an inadhesive section between the films 1001, which has squashed state before introduction of liquid thereinto and is expanded to be a solution chamber after introduction of liquid thereinto.

A swab to which cells of a subject have been attached is inserted into the cell accepting section 101. Then, lysis solution is transferred from the lysis solution chamber 102 to the cell accepting section 101 so that the subject cells are detached from the swab. Furthermore, the lysis solution is transferred from the cell accepting section 101 to the lysis reaction chamber 103 and the lysis solution is heated. Herein, liquid transfer on the microchip 1000 will be explained in detail below. Compressed air and the like are injected into pressurization paths so that flow paths thorough which the lysis solution is not transferred have a closed state during liquid transfer. Therefore, for example, in a case where the cell accepting section 101 is pressurized so that the lysis solution in the cell accepting section 101 is transferred to the lysis reaction chamber 103, the lysis solution never flows backward to the lysis solution chamber 102.

Accordingly, preparation of the sample solution may be carried out on the microchip 1000. In addition, in a case where liquid transfer on the microchip 1000 is automatically controlled by a controlling apparatus, the preparation of the sample solution may be carried out automatically with simple operation that a swab to which subject cells are attached is inserted into the cell accepting section 101. That is, operator's operation is decreased.

Embodiment 1

Figure 2:
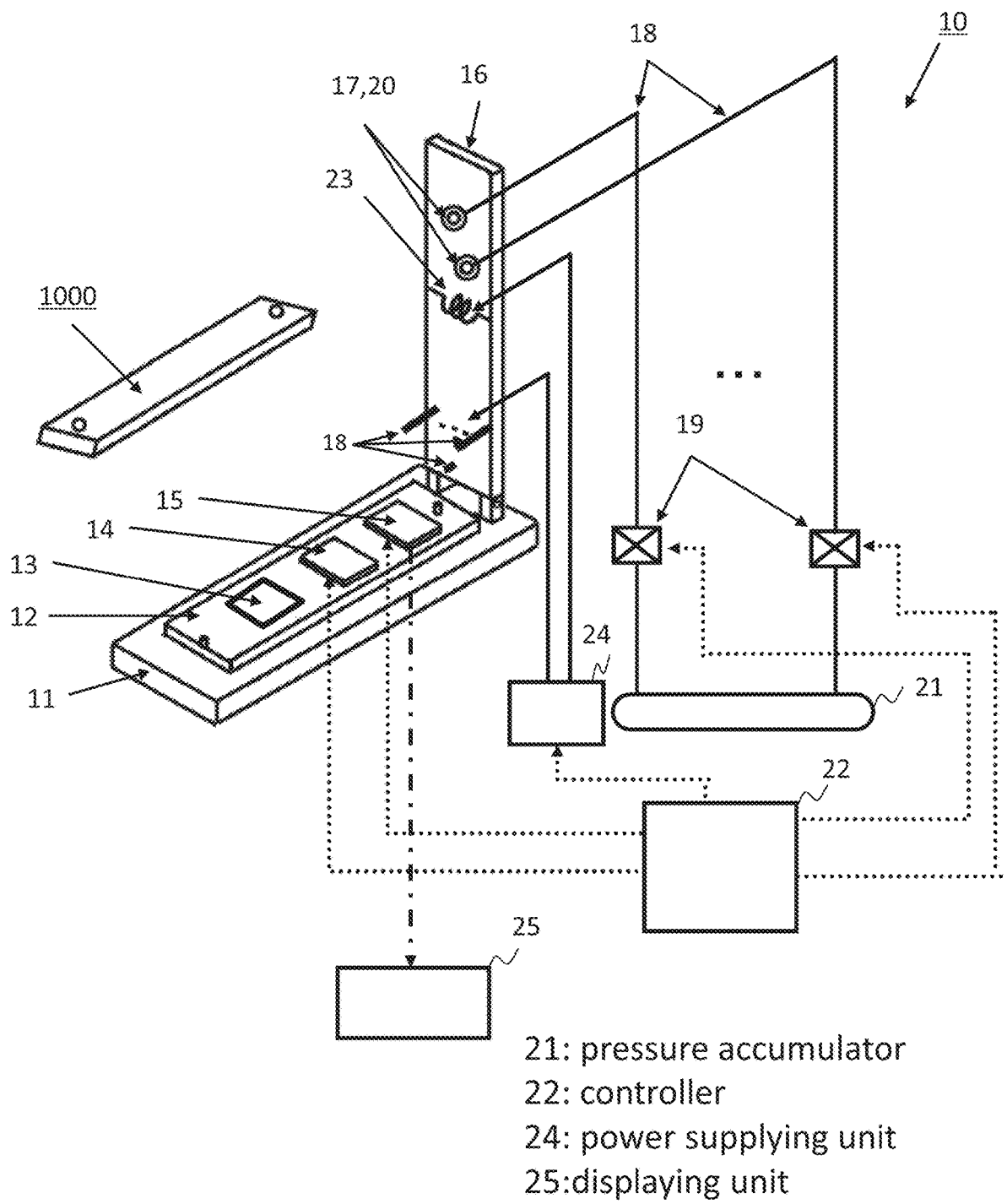
FIG. 2 is a diagram showing an example of a microchip controlling apparatus.

A microchip, microchip controlling apparatus and microchip controlling system will be explained below with a specific example along with reference to drawings. As shown in FIG. 2, in the microchip controlling apparatus 10, a table 12 is arranged on a base station 11. A sample solution preparing unit 13, PCR unit 14, electrophoresis unit 15 are arranged on the table 12. In addition, the base station 11 and lid 16 are connected via a hinge so that the lid 16 may be opened and closed.

The microchip 1000 is loaded at a predetermined position on the table 12 by fitting pins arranged on the table 12 with pin holes arranged on the microchip 1000. When the lid 16 is closed under the state where the microchip 1000 is loaded on the table 12, a sample solution preparing section 100 of the microchip 1000 contacts with a sample solution preparing unit 13. In addition, a DNA extraction/PCR section 200 contacts with a PCR unit 14 and an electrophoresis section 300 contacts with an electrophoresis unit 15. Furthermore, electrodes are inserted into electrode chambers of the microchip 1000 via electrode holes arranged on the microchip 1000.

A plurality of pressurizing holes 17 is arranged on the lid 16. Regions on the lid 16 corresponding to these pressurizing holes 17 are perforated, and the pressurizing holes 17 are connected with a solenoid valve 19 via tubes 18. In addition, when the lid 16 is closed, the pressurizing holes 17 and a variety of control holes on the microchip 1000 are to be connected. Herein, it is preferable that the pressurizing holes 17 contacts with the control holes via interposed sealing mechanisms, such as O-rings 20.

Pressurizing medium, such as compressed air, is stored in a pressure accumulator 21, and a controller 22 controls the solenoid valve 19 so that the pressurizing medium is injected into/ejected from the control holes on the microchip 1000 via the pressurizing holes 17. Herein, internal pressure of the pressure accumulator 21 is controlled by pressure sensor, pump and the like, not shown, so as to be kept at a predetermined pressure.

A DNA extracting unit 23 is arranged on the lid 16 for extracting sample DNA or template DNA from sample solution. For example, in a case where the sample DNA is extracted with magnetic beads (silica), the DNA extracting unit 23 comprises neodymium magnets to which magnetic beads are attached. Under control by controller 22, the DNA extracting unit 23 brings a magnet (for example, neodymium magnet) near the DNA extracting section 244 or takes the magnet away from DNA extracting section 244.

A sample solution preparing unit 13 and PCR unit 14 comprise temperature sensor, heat conductor, Peltier element (thermoelectric element), heat releasing plate and the like. The sample solution preparing unit 13 executes lysis reaction by heating lysis solution comprising subject's cells, and the PCR unit 14 executes PCR.

An electrophoresis unit 15 is a mechanism for executing capillary electrophoresis and detection of fluorescent label, comprising an excitation device, such as halogen lamp, mercury lamp, laser beam, filters and a camera as a fluorescent label detecting mechanism. When capillary electrophoresis is started by applying DC voltage to the electrodes via a power supplying unit 24, the electrophoresis unit 15 monitors fluorescent label flowing through capillaries and outputs detection result of a graph showing change in fluorescence intensity in a time dependent manner.

Herein, the controller 22 may be also realized with computer program which makes a computer installed in the microchip controlling apparatus 10 to execute a process by the controller 22, explained below in detail, with its hardware.

Figure 3:
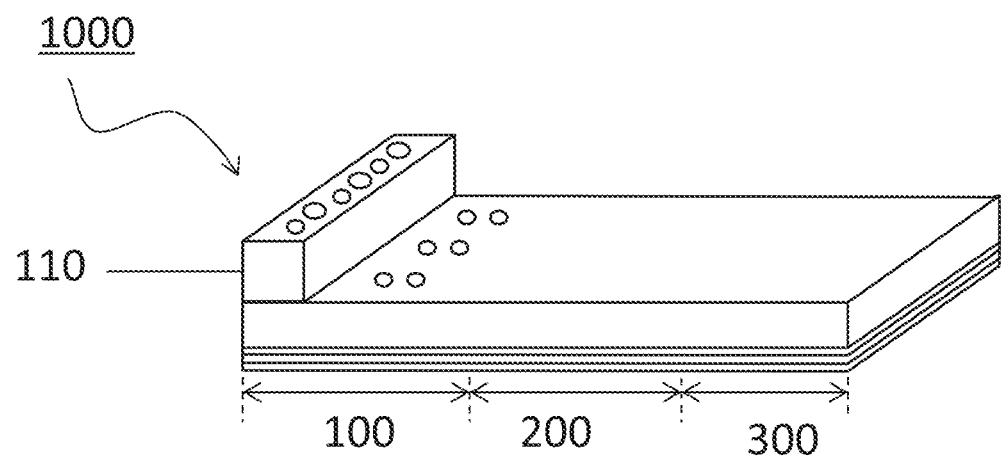
FIG. 3 is a diagram showing an example of a microchip.

As shown in FIG. 3, the microchip 1000 comprises a sample solution preparing section 100, a DNA extraction/PCR section 200 and an electrophoresis section 300. Although FIG. 3 shows a microchip 1000 comprising 3 cascade constructions in which 3 samples are simultaneously processed, one cascade construction will be explained below for simplification of explanation.

The sample solution preparing section 100 and the DNA extraction/PCR section 200 are so constructed that a plurality of elastic sheets are vertically sandwiched by resin plates. The elastic sheets are adhered each other excepting for a part, the inadhesive sections may be expanded by injection of medium, such as liquid and air. The sample solution preparing section 100 comprises a platform-shaped projecting part 110 having a predetermined height on a resin plate.

It is preferable that the elastic sheets have an elasticity, heat resistance and acid/alkali resistance. In addition, it is preferable that the resin plates have hardness to an extent that extension of the elastic sheets may be restricted. Herein, it may be also realized that the lower resin plate is placed on the base station 11 of the microchip controlling apparatus 10. A variety of control holes, such as medium charging/discharging holes, are arranged on the microchip 1000.

Figure 4:
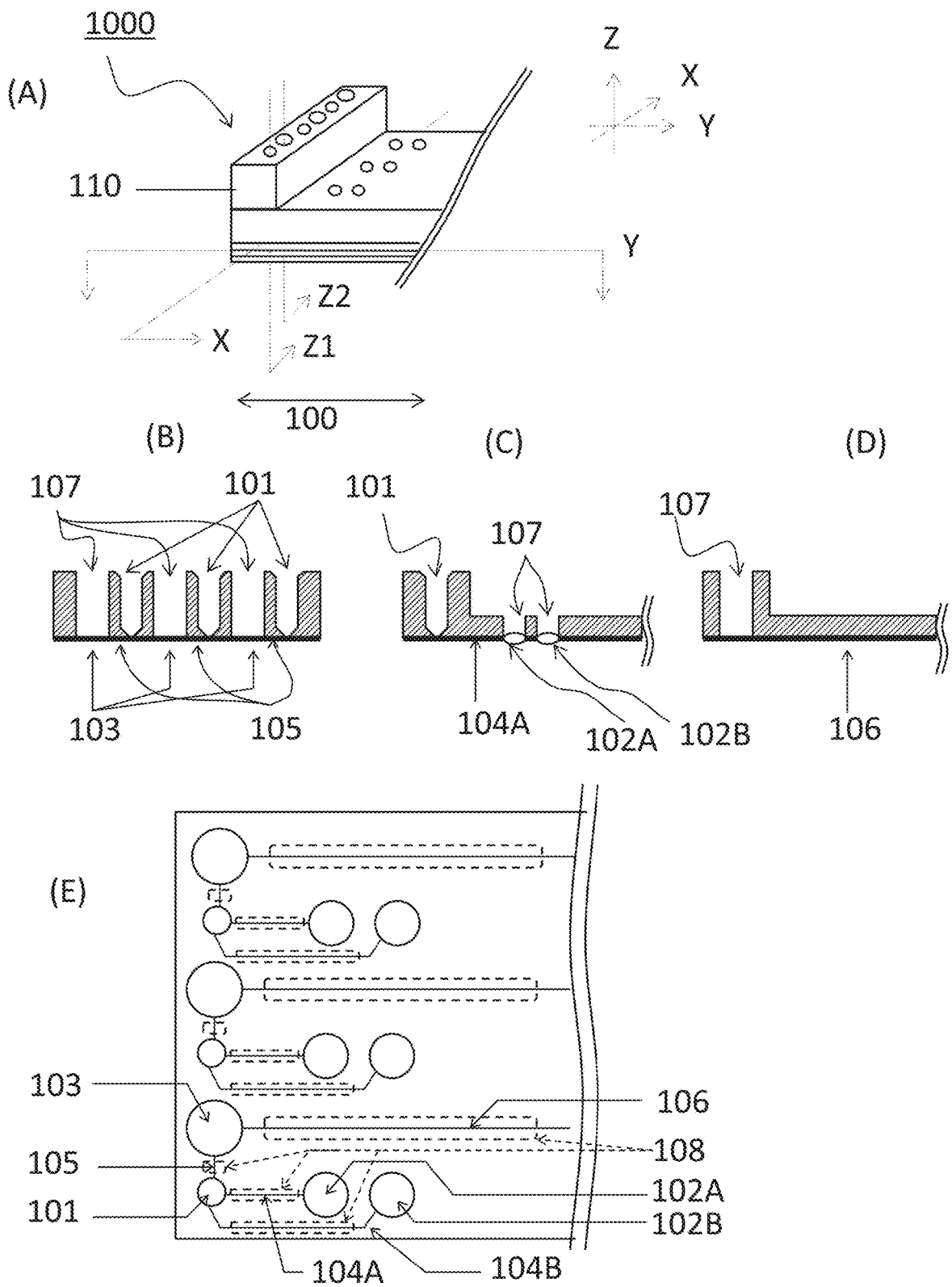
FIG. 4 is a diagram showing an example of a sample solution preparing section.

FIG. 4(A) is a perspective view of the sample solution preparing section 100 and FIGS. 4(B), 4(C), 4(D), 4(E) are X axis sectional view, Z1 axis sectional view, Z2 axis sectional view, Y axis sectional view, respectively. As shown in FIG. 4, the sample solution preparing section 100 comprises cell accepting sections 101, lysis solution chambers 102A, 102B and lysis reaction chambers 103, which are connected with flow paths 104A, 104B, 105 and 106. Pressurization paths 108 are arranged below the flow paths 104A, 104B, 105, 106 respectively. The flow paths 104A, 104B, 105, 106 may be closed by injection of pressurizing medium into the pressurization paths 108 or opened by cancelling the injection. Herein, in FIGS. 4(A), 4(B), 4(C) and 4(D), the pressurization paths 108 are omitted for clarification.

The cell accepting section 101 is arranged on the projecting part 110, comprising an opening part at upper side, and reaching the elastic sheets arranged at bottom part of the projecting part 110 through the projecting part 110. The cell accepting section 101 is communicated with lysis solution chambers 102A and 102B respectively via first flow paths 104A and 104B arranged between the elastic sheets, and communicated with a lysis reaction chamber 103 via a second flow path 105 arranged between the elastic sheets in the same manner. For example, a swab to which subject's cells are attached is inserted from upper side of the opening part into the cell accepting section 101.

Herein, it is preferable that the upper opening part of the cell accepting section 101 has a taper-shape whose diameter is enlarged at upper side, thereby, for example, in a case where abundant saliva from a subject is attached to a swab, a risk of overflow of liquid from the cell accepting section 101 is reduced. On the other hand, it is preferable that the cell accepting section 101 whose diameter is reduced at lower side, thereby, for example, even in a case of small amount of subject's saliva attached to a swab, subject's cells may be collected efficiently.

Figure 5:
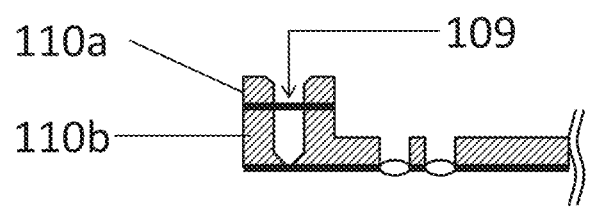
FIG. 5 is a diagram showing an example of the sample solution preparing section.

Furthermore, an anti-splash mechanism may be arranged on the cell accepting section 101 for preventing splash of lysis solution. As shown in FIG. 5, for example, an anti-splash film 109 having slits is arranged to cover the cell accepting section 101. Thereby, the risk of attaching of the lysis solution to the microchip controlling apparatus 10 is reduced, thus contamination (contamination of foreign substance) may be prevented. Herein, in a case where the anti-splash film is arranged, the projecting part 110 is so constructed that it may be separated into an upper projecting part 110a and a lower projecting part 110b, and two projecting parts 110a and 110b sandwich the anti-splash film 109.

In addition, a sealing mechanism, such as O-ring 20, may be arranged on edge of upper opening part of the cell accepting section 101. Thereby, unevenness in the microchip controlling apparatus 10 at the side of lid 16 may be reduced, resulting in easiness in cleaning.

The lysis solution chamber 102A stores lysis solution for lysis of the cells (for example, SDS/LiOAc solution (sodium dodecyl sulfate/lithium acetate solution)) at gap between the elastic sheets in advance, and the lysis solution chamber 102B previously stores nuclease inhibitors, such as proteinase K, in advance. Pressurizing holes 107 are arranged at upper side of the lysis solution chambers 102A and 102B. When pressurizing medium, such as compressed air, is applied thereto via the pressurizing holes 107, the lysis solution chamber 102A and 102B are compressed and lysis solution and the like is transferred to the cell accepting section 101 through the first flow paths 104A, 104B.

Figure 6:
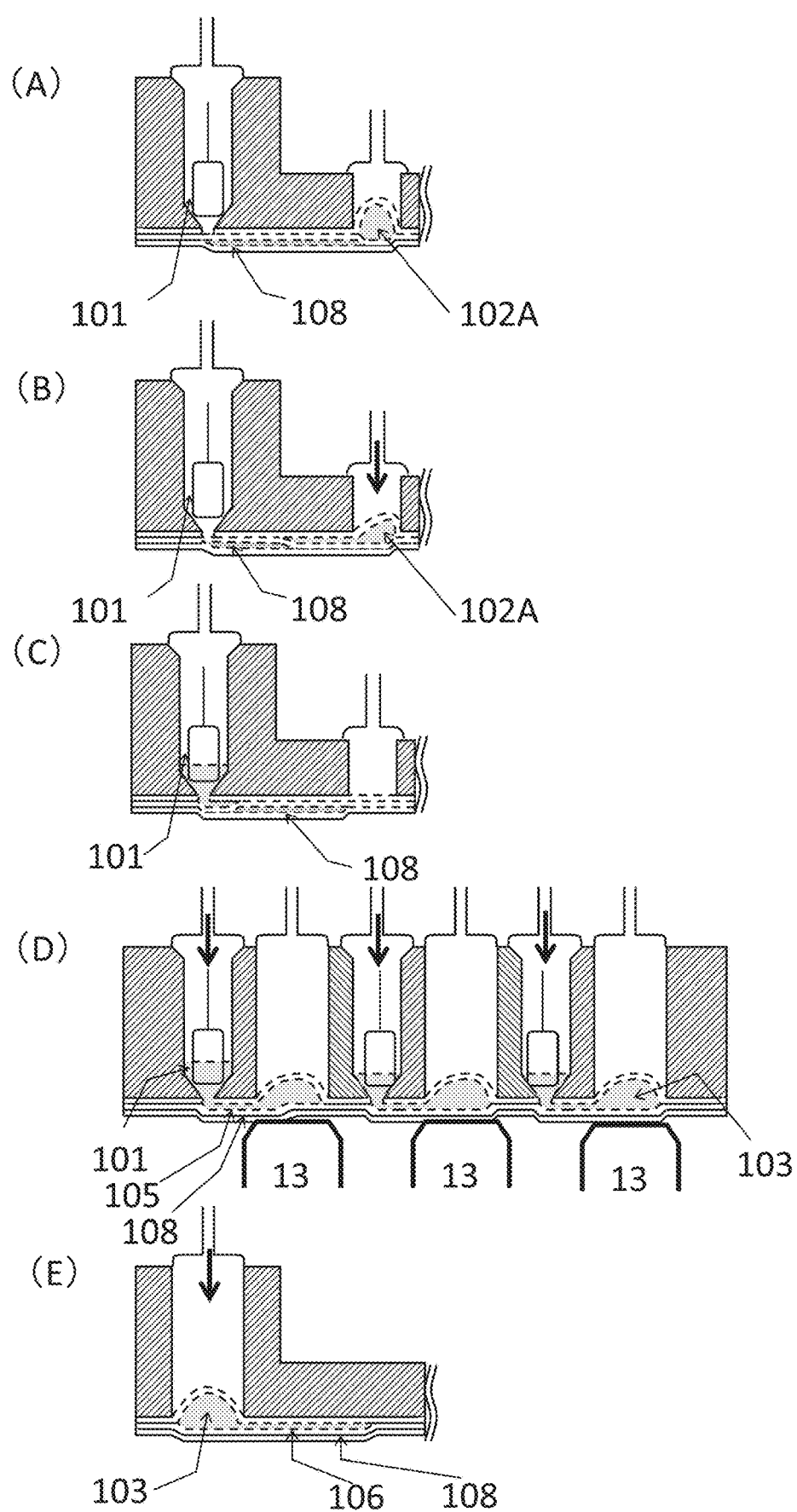
FIG. 6 is an explanatory diagram of liquid transferring mechanism on the microchip.

Herein, liquid transferring mechanism in the microchip 1000 is explained with a concrete example. FIGS. 6(A) to 6(C) are Z1 axis sectional views of the microchip 1000, FIG. 6(D) is X axis sectional view, and FIG. 6(E) is Z2 axis sectional view. As shown in FIG. 6(A), the lysis solution chamber 102A formed between the elastic sheets stores lysis solution. A pressurization path 108 arranged below a first flow path 104A is expanded by injection of pressurizing medium so that the first flow path 104A is closed.

Then, as shown in FIG. 6(B), when pressure with pressurizing medium in the pressurization path 108 is cancelled and the lysis solution chamber 102A is pressurized with pressurizing medium, lysis solution pushed out from the lysis solution chamber 102A reaches a cell accepting section 101 through the first flow path 104A. At that time, the second flow path 105 has been closed, thus the lysis solution stops at the cell accepting section 101.

Then, as shown in FIG. 6(C), pressurizing medium is injected into the pressurization path 108 again so as to pressurize it, the first flow path 104A is closed. Accordingly, the liquid transfer in the microchip 1000 is carried out.

As shown in FIG. 6(D), when liquid flows into the lysis reaction chamber 103 from the cell accepting section 101, it is expanded to be formed. At that time, first flow paths 104A, 104B and third flow path 106 have been closed and second flow path 105 has been opened. Upper side of the lysis reaction chamber 103 is opened so that pressurizing medium may be injected or ejected. In addition, lower side of the lysis reaction chamber 103 is also opened so that a part of sample solution preparing unit 13 (specifically, a heat conductor conducting heat from Peltier element) contacts thereto. As stated above, the lysis reaction chamber 103 between the elastic sheets has a construction to be expanded by inflow of liquid, thus when the lysis reaction chamber 103 is expanded, the lysis reaction chamber 103 closely contacts to the sample solution preparing unit 13. In addition, the lysis reaction chamber 103 is communicated with a DNA extracting section 244 via the third flow path 106. Thus, in a case where second flow path 105 is closed, the third flow path 106 is opened and, then lysis reaction chamber 103 is pressurized after heating treatment, sample solution in the lysis reaction chamber 103 flows into a DNA extraction/PCR section 200 through the third flow path 106.

Herein, it is preferable that capacity of the lysis reaction chamber 103 is less than total volume of solution which has been injected into the lysis solution chambers 102A, 102B. Due to such construction, volume of sample solution may be restricted up to the capacity of the lysis reaction chamber 103 and contamination of air into the lysis reaction chamber 103 may be also prevented.

Furthermore, solution may be transferred forward and back (i.e. being shuttled) between the cell accepting section 101 and the lysis reaction chamber 103. Thereby, lager numbers of cells may be collected from a swab.

Figure 7:
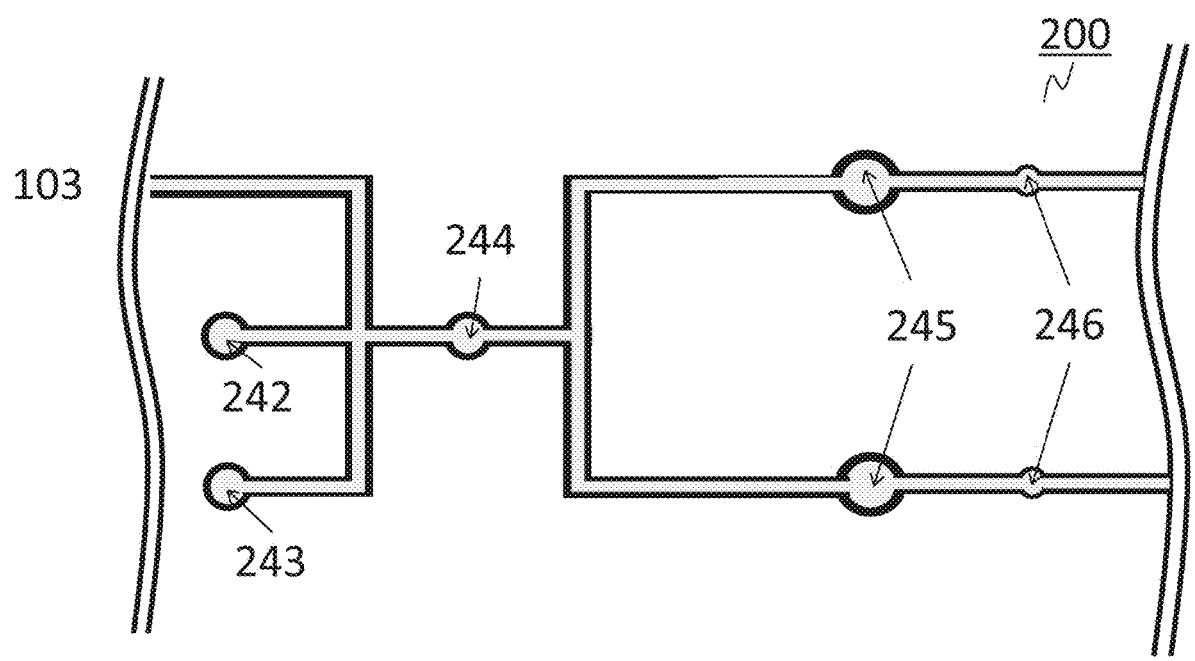
FIG. 7 is a diagram showing an example of a DNA extraction/PCR section.

FIG. 7 shows a schematic plan view of the DNA extraction/PCR section 200. The DNA extraction/PCR section 200 comprises a wash buffer chamber 242, an elution buffer chamber 243, a DNA extracting section 244, a PCR section 245, and a volume determination section 246. The wash buffer chamber 242 and elution buffer chamber 243 have the same construction as the lysis solution chambers 102A and 102B, wash buffer and elution buffer are stored in advance. Herein, the wash buffer is, for example, Tris (tris (hydroxymethyl) aminomethane) buffer, and the elution buffer contains polymerase for primer extension reaction and dNTP mix (mixture or deoxyribonucleotide triphosphates).

The DNA extracting section 244 is a mechanism for extraction of DNA from sample solution. For example, magnetic beads (silica) are stored in the DNA extracting section 244 in advance, sample DNA is extracted from the sample solution under control by the controller 22 and the DNA extracting unit 23.

DNA extraction process will be specifically explained. The microchip controlling apparatus 10 comprises a neodymium magnet as the DNA extracting unit 23 and magnetic beads coated with silica are stored in the DNA extracting section 244 in advance. The microchip controlling apparatus 10 transfers sample solution from the lysis reaction chamber 103 to the DNA extracting section 244 so that DNA is attached to the magnetic beads (silica) stored in the DNA extracting section 244. Then the DNA is extracted by washing the magnetic beads with wash buffer in the wash buffer chamber 242. Herein, the microchip controlling apparatus 10 discharges the sample solution and wash buffer via a drainage port (not shown), then the magnetic beads are attached to the neodymium magnet so that the magnetic beads are prevented from being discharged together with the sample solution and wash buffer.

The DNA extraction method may be modified by reference to ordinary protocols so as to, for example, add the number of washing. Furthermore, the DNA extraction method is not limited to a method with the magnetic beads, thus, for example, a method with columns may be applied.

The PCR section 245 executes PCR under temperature control by the PCR unit 14. Specifically, primer sets are stored in the PCR section 245 in advance, and desired nucleic acid sequence in sample DNA (template DNA) extracted by the DNA extracting section 244 is amplified by reaction due to the polymerase contained in the elution buffer.

The volume determination section 246 is a mechanism for determining the volume of the solution containing amplicon. Specifically, the volume determination section 24 has a construction smaller than the PCR section 245, liquid transfer is accomplished under a state where the solution in the PCR section 245 is not completely transferred to the volume determination section 246. In other words, the microchip controlling apparatus 10 determines the volume of the solution containing amplicon by leaving a part of solution in the PCR section 245.

Figure 8:
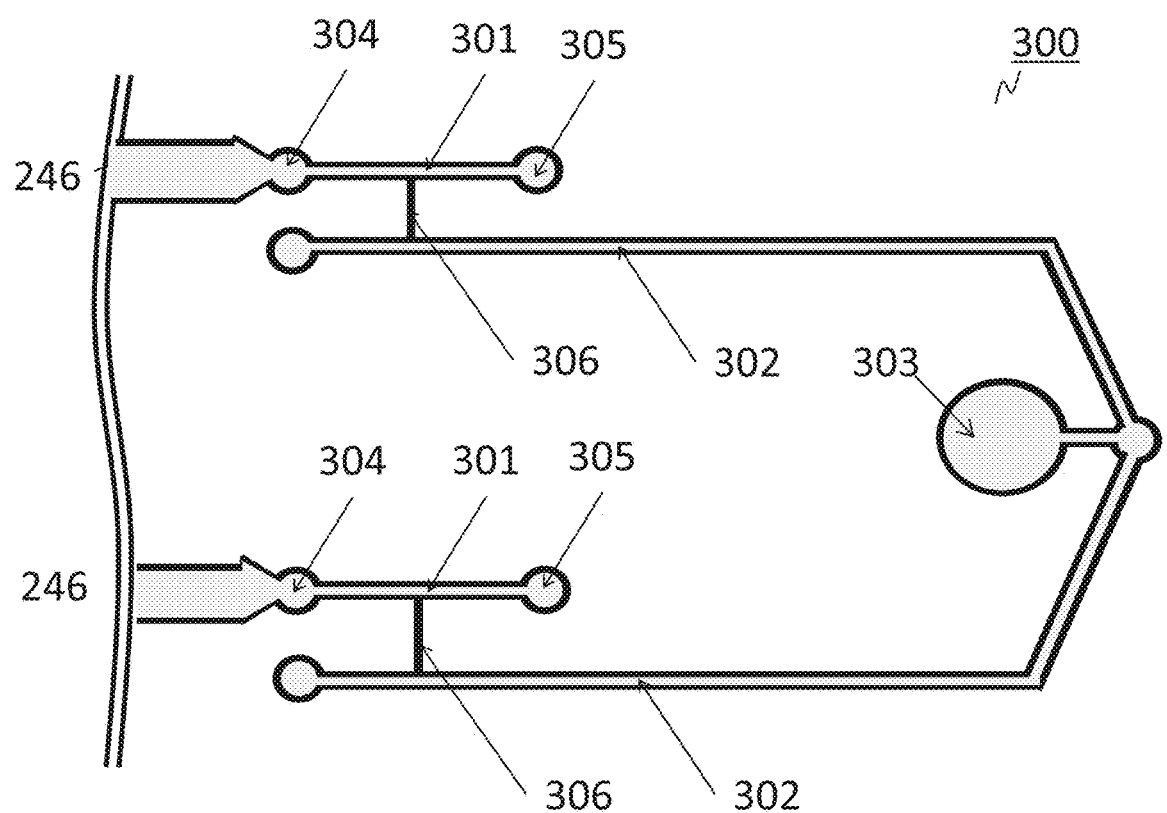
FIG. 8 is a diagram showing an example of an electrophoresis section.

As shown in FIG. 8, the electrophoresis section 300 comprises sample flow paths 301, capillaries 302, a polymer chamber 303. Specifically, the sample flow path 301 is communicated with the volume determination section 246 via a electrode chamber 304 and communicated with a reservoir 305 at the opposite side end. The reservoir 305 is a mechanism for prevention of overflow of sample flowing into the sample flow path 301. The capillary 302 is communicated with the polymer chamber 303 via the electrode chamber 304. In addition, the sample flow path 301 and the capillary 302 extend in parallel and are communicated with a bridge 306 orthogonal to the sample flow path 301 and the capillary 302. Electrodes arranged on the lid 16 are inserted into the electrode chambers 304.

The microchip controlling apparatus 10 fills up the capillary 302 and bridge 306 with polymer and executes electrophoresis subsequent to sample injection. Upon the electrophoresis, the microchip controlling apparatus 10 monitors labels flowing in the capillary with the electrophoresis unit 15 in order to output detection result via a displaying unit 25, in which change in fluorescence intensity is graphed in a time dependent manner.

A part or entire of embodiment above may be described as the following modes, but not limited thereto.

(Mode 1)
A microchip configured to comprise:
  a cell accepting section accepting cells obtained from a subject,
  a lysis solution chamber storing lysis solution for lysis of the cells, and
  a lysis reaction chamber in which lysis reaction of the cells is executed.

(Mode 2)
The microchip according to Mode 1, wherein
  the cell accepting section comprises opening parts in vertical direction respectively, a stick tool to which the cells are attached is inserted thereinto from an upper opening part, and a lower opening part is communicated with the lysis solution chamber and the lysis reaction chamber.

(Mode 3)
The microchip according to Mode 1 or 2, wherein
  the upper opening part has a taper shape whose diameter is enlarged at upper side, and the lower opening part has a taper shape whose diameter is reduced at lower side.

(Mode 4)
The microchip according to any one of Modes 1 to 3, wherein
  the cell accepting section has an anti-splash mechanism for preventing slashing of lysis solution.

(Mode 5)
The microchip according to any one of Modes 1 to 4, wherein
  the lysis reaction chamber is expanded by liquid flowing from the cell accepting section.

(Mode 6)
The microchip according to Mode 5, wherein
  the volume of the lysis reaction chamber is smaller than the volume of the cell accepting section.

(Mode 7)
The microchip according to any one of Modes 1 to 6, wherein
  the microchip comprises a sealing mechanism providing a sealing state between a microchip controlling apparatus controlling the microchip and the microchip.

(Mode 8)
A microchip controlling apparatus configured to comprise:
  a microchip loading unit on which loaded is a microchip comprising a cell accepting section accepting subject's cells, a lysis solution chamber storing lysis solution for lysis of the cells, and a lysis reaction chamber in which lysis reaction of the cells is executed;
  a first lysis solution transferring unit for transferring the lysis solution from the lysis solution chamber to the cell accepting section;
  a second lysis solution transferring unit for transferring the lysis solution containing cells from the cell accepting section to the lysis reaction chamber; and
  a lysis reaction unit heating lysis solution containing the cells in the lysis reaction chamber so as to execute the lysis reaction.

(Mode 9)
The microchip controlling apparatus according to Mode 8, wherein the second lysis solution transferring unit transfers the lysis solution forward and back between the lysis solution chamber and the cell accepting section at a plurality of times.

(Mode 10)
A microchip controlling system configured to comprises:
  a microchip comprising
  a cell accepting section accepting subject's cells,
  a lysis solution chamber storing lysis solution for lysis of the cells, and
  a lysis reaction chamber in which lysis reaction of the cells is executed; and
  a microchip controlling apparatus comprising
  a first lysis solution transferring unit transferring part for transferring
  the lysis solution from the lysis solution chamber to the cell accepting section,
  a second lysis solution transferring unit transferring part for transferring the lysis solution containing cells from the cell accepting section to the lysis reaction chamber,
  a lysis reaction unit heating lysis solution containing the cells in the lysis reaction chamber so as to execute the lysis reaction.

Herein, Mode 8 and Mode 10 may be developed to Mode 2 to Mode 7 like as Mode 1.

The disclosure in the Patent Literature above is incorporated into the present application by reference. The particular exemplary embodiments or examples may be modified or adjusted within the scope of the entire disclosure of the present invention, inclusive of claims, based on the fundamental technical concept of the invention. In addition, a variety of combinations or selection of elements disclosed herein, inclusive each element in each claim, each element in each example, each element in each drawing etc., may be made within the context of entire disclosure of the present inventions. That is, the present invention may cover a wide variety of modifications or corrections that may be made by those skilled in the art in accordance with the entire disclosure of the present invention, inclusive of claims, and the technical concept of the present invention. Particularly, the numerical value or range described in the present application should be interpreted so that optional numerical value or smaller range within the range is specifically described even in a case where there are no specific disclosures.

What is claimed is:

1. A system comprising:
    a microchip;
    a table on which the microchip is loaded;
    a controller; and
    a lysis reaction unit,
    wherein the microchip comprises:
    a cell accepting section accepting cells obtained from a subject;
    a lysis solution chamber storing a lysis solution for lysis of the cells;
    a lysis reaction chamber in which lysis reaction of the cells is executed;
    a first flow path communicating the cell accepting section directly to the lysis solution chamber; and
    a second flow path communicating a bottom opening of the cell accepting section directly to the lysis reaction chamber,
    wherein the lysis solution chamber, the lysis reaction chamber, the first flow path and the second flow path are configured as inadhesive sections between adhesively laminated elastic films;
    wherein the first flow path is configured to allow the lysis solution stored in the lysis solution chamber to flow into the cell accepting section,
    wherein the second flow path is configured to allow the lysis solution stored in the cell accepting section to flow into the lysis reaction chamber together with the cells and also allow the lysis solution stored in the lysis reaction chamber to flow back into the lysis reaction chamber,
    wherein the lysis reaction chamber is configured to expand when the lysis solution is transferred from the cell accepting section into the lysis reaction chamber together with the cells and to have a capacity that is smaller than a capacity of the cell accepting section such that the lysis solution transferred into the lysis reaction chamber is restricted up to a capacity of the lysis reaction chamber,
    wherein the controller is configured to control transferring of the lysis solution from the lysis solution chamber to the cell accepting section, transferring of the lysis solution containing cells from the cell accepting section to the lysis reaction chamber, and transferring of the lysis solution forward and back between the lysis solution chamber and the cell accepting section at a plurality of times,
    wherein the lysis reaction unit is configured to heat lysis solution containing the cells in the lysis reaction chamber so as to execute the lysis reaction.

\* \* \* \* \*